United States Patent [19]

Gehrer et al.

[11] Patent Number: 5,410,089
[45] Date of Patent: Apr. 25, 1995

[54] PREPARATION OF DIHYDROXYACETONE

[75] Inventors: Eugen Gehrer, Ludwigshafen; Wolfgang Harder, Weinheim; Herbert Vogel, Ludwigshafen; Bernhard Knuth, Laumersheim; Klaus Ebel, Ludwigshafen; Carsten Groening, Ludwigshafen, all of Germany

[73] Assignee: BASF Aktiengesellschaft, Ludwigshafen, Germany

[21] Appl. No.: 54,814

[22] Filed: Apr. 29, 1993

[30] Foreign Application Priority Data

May 4, 1992 [DE] Germany .................. 42 14 808.1

[51] Int. Cl.$^6$ ............................................. C07C 45/00
[52] U.S. Cl. .................................................. 568/388
[58] Field of Search ........................................ 568/388

[56] References Cited

FOREIGN PATENT DOCUMENTS

| 219317 | 4/1987 | European Pat. Off. . |
| 0306215 | 3/1989 | European Pat. Off. . |
| 410613 | 1/1991 | European Pat. Off. . |
| 474387 | 3/1992 | European Pat. Off. ............ 568/388 |
| 480646 | 4/1992 | European Pat. Off. ............ 568/388 |

OTHER PUBLICATIONS

Tetrahedron Lett. 21, pp. 4517–4520 (1980).
J. Am. Chem. Soc. 106, pp. 4829–4832 (1984).
Liebigs Ann. Chem. 708, pp. 155–169 (1967).

Primary Examiner—Alan Siegel
Attorney, Agent, or Firm—John H. Shurtleff

[57] ABSTRACT

A process for preparing dihydroxyacetone by condensation, catalyzed by a thiazolium ylide, of formaldehyde, wherein the reaction is carried out in a system composed of an aqueous phase and at least one organic liquid phase.

13 Claims, No Drawings

PREPARATION OF DIHYDROXYACETONE

The present invention relates to a process for preparing dihydroxyacetone by condensation, catalyzed by thiazolium ylides, of formaldehyde.

Formoin condensation, catalyzed by thiazolium ylides, of formaldehyde to give dihydroxyacetone (DHA) in an anhydrous medium was described for the first time by Castells (Tetrahedron Lett. 21 (1980) 4517).

Matsumoto et al. (J. Am. Chem. Soc. 106 (1984) 4829) systematically investigated this reaction in various solvents and obtained good results on use of anhydrous solvents such as ethanol, butanol, dioxane, diethylene glycol, dimethyl ether, ethyl propionate, dimethyl sulfoxide, dimethylformamide and heptane. Only when water was used was there no yield of DHA.

According to EP-A 306 215, the conversion of formaldehyde, catalyzed by thiazolium ylides, into DHA must be carried out in an essentially anhydrous reaction medium, by which is meant a water content of less than 0.4% by weight, preferably of less than 0.1% by weight. This is also the reason why dry, anhydrous formaldehyde is used as starting material in this process.

According to EP-A 410 613, it is also possible to generate catalytically active thiazolium ylides from thiazolium salts by dissolving the latter in an organic solvent and extracting the anions thereof from the organic solution by means of water. After the extraction is complete, the aqueous and organic phases are separated. The residual amounts of water dissolved in the organic medium are subsequently removed with a portion of the organic solvent by azeotropic distillation. In this case, the condensation of the anhydrous formaldehyde dissolved in the organic phase to give DHA starts only when the water content of the reaction medium has fallen to 0.1% by weight.

The reason for the poor results with the said reaction in the presence of water is presumably that there is nucleophilic attack by the hydroxide ions present in the aqueous medium on the catalytic thiazolium compounds in position 2 of the thiazolium ring, which not only blocks the catalytically active center of the compound but also eventually leads to ring opening and irreversible decomposition of the catalytic compound.

In virtually all industrial preparation processes, formaldehyde is obtained as aqueous solution. The production of anhydrous formaldehyde, e.g. in the form of dried paraformaldehyde solutions or gaseous formaldehyde, entails considerable additional costs which greatly impair the economics of processes for preparing DHA and, in particular, the products derived from it: glycerol (EP-A 306 215) and 1,2-propanediol (German Patent Application No. P 41 38 792.9).

It is an object of the present invention to find a process with which it is possible to prepare DHA from crude aqueous formaldehyde solutions without further workup by means of thiazolium ylide catalysts.

We have found that this object is achieved by a process for preparing dihydroxyacetone by condensation, catalyzed by a thiazoliumylide, of formaldehyde, wherein the reaction is carried out in a system composed of an aqueous phase and at least one organic liquid phase.

Thus, the reaction system used in the process according to the invention is one composed of at least one organic liquid phase which is immiscible with water and of an aqueous phase. In this case the catalyst, for example a thiazolium ylide, is essentially present in the organic phase, whereas the formaldehyde to be condensed preferentially dissolves in the aqueous phase. A simplified description of the chemical processes taking place in the process according to the invention is that the formaldehyde is transported, possibly with the assistance of the organic solvent, from the aqueous phase into the organic phase and there condensed by the catalyst, which is essentially dissolved in the organic phase, to give DHA, which subsequently migrates into the aqueous phase from which it can be isolated. The process according to the invention thus takes place with phase-transfer catalysis.

To carry out the process according to the invention, the formaldehyde is generally used in the form of its aqueous solution. However, the formaldehyde can also be introduced in another form, for example as gaseous formaldehyde/water vapor mixture.

The catalysts for the condensation of formaldehyde are, according to the invention, essentially in the organic phase which is immiscible with water. This organic phase is generally an organic solvent, but can also be a liquid organic phase in which the catalyst is dissolved and which is absorbed onto, and firmly adherent to, an organic or inorganic support material. It is furthermore possible for the catalyst itself to be used as organic phase, for example in the form of its melt.

Suitable organic solvents for the process according to the invention are a large number of organic solvents which are immiscible with water, for example higher alcohols, N,N-dialkylformamides, N-alkylpyrrolidones, hydrocarbons or halogenated hydrocarbons. Particularly preferably used are higher alcohols, especially $C_5$–$C_{30}$ alcohols, and N,N-dialkylformamides such as N,N-dipropylformamide, N,N-dibutylformamide, N,N-dipentylformamide etc. Particularly advantageous alcoholic solvents are $C_6$–$C_{22}$ alcohols such as n-hexanol, cyclohexanol, 2-ethylhexanol, n-octanol, nonanols, decanols, dodecanols, hexadecanols and eicosanols, and of these the alcohols which are in turn preferably used, because they are easily obtained industrially, are those derived from naturally occurring fatty acids or, like 2-ethylhexanol, are produced in large amounts for other industrial uses and are therefore available at reasonable cost. It is equally possible to use mixtures of various organic solvents which are insoluble in water with good results.

Supported liquid organic phases can be prepared, for example, by applying a solution of the catalyst in a lipophilic organic solvent, with or without the addition of a volatile auxiliary solvent, onto a support material of large surface area. The techniques which can be used for this are all those familiar for the preparation of support materials for gas chromatography.

If lipophilic catalysts which are substituted by, for example, long-chain lipophilic radicals, e.g. long-chain alkyl radicals, are used, these catalysts can themselves form the liquid organic phase in both the presence and the absence of an organic solvent.

However, in general, and preferably, organic solvents are used as organic phase in the process according to the invention, the ratio of aqueous phase to organic phase usually being from 0.01 to 5, preferably from 0.1 to 1 and particularly preferably from 0.2 to 0.5 by volume. The use of larger amounts of water is likewise possible but this generally has no further advantages.

The catalysts expediently used in the process according to the invention contain a thiazolium ring which is unsubstituted in position 2, for example thiazolium ylides of the formula I

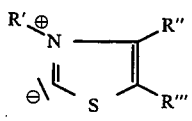

Isolation of these ylides results, depending on the mode of generation of the thiazolium ylides, in dimers of the formula Ia

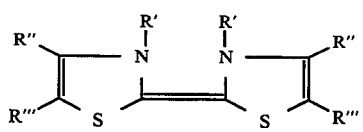

or alcohol adducts of the formula Ib

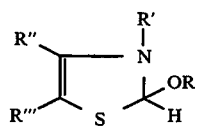

The compounds of the formula Ia can preferably be isolated from thiazolium ylide solutions which have been obtained, for example, by deprotonation of the relevant thiazolium salts using amines, whereas the compounds Ib can preferably be obtained from thiazolium ylide solutions which have been generated, for example, by reacting N-formyl-N-alkyl-o-mercaptoaniline derivatives with orthoformates. The compounds Ia and Ib are stable and can be obtained as crystals, and Ib, in particular, can be used as stable form for storing the ylides I.

The only factor important for the catalytic activity of the thiazolium compounds used as catalysts is that the thiazolium ylides prepared therefrom are unsubstituted in position 2 of the thiazolium ring. Otherwise, the thiazolium ylide catalysts can be substituted by any suitable substituents R', R" or R'''. It is possible to use, for example, thiazolium ylides of the formula Ic

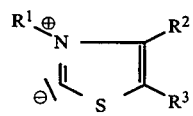

or benzothiazolium ylides Id

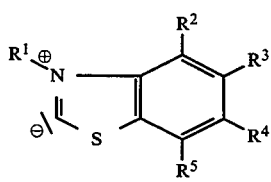

where $R^1$ is, for example, $C_1$–$C_{30}$ alkyl, preferably $C_2$–$C_{20}$ alkyl, or haloalkyl which has a corresponding number of carbons and which can preferably contain fluorine or chlorine as halogen, $C_1$–$C_{30}$ alkylene which is bonded to a polymeric support, $C_7$–$C_{20}$ aralkyl, preferably $C_7$–$C_{12}$ aralkyl, especially benzyl, or aryl such as phenyl or naphthyl. $R^2$ to $R^5$ can in principle be of any suitable type as long as they are inert under the reaction conditions. Thus, $R^2$, $R^3$, $R^4$ and $R^5$ can be, for example, identical or different and each be hydrogen, halogen, $C_1$–$C_{20}$ alkyl or alkoxy, preferably $C_1$–$C_4$ alkyl, $C_1$–$C_{20}$, preferably $C_2$–$C_4$ acylamino, $C_7$–$C_{12}$ aralkyl, preferably benzyl, and or phenyl or naphthyl. $R^1$, $R^2$, $R^3$, $R^4$ and $R^5$ can, if required, also have substituents which are inert under the reaction conditions, such as alkyl, alkoxy, halogen, $C_2$–$C_{10}$ dialkylamino, $C_1$–$C_{10}$ alkylthio, nitro or cyano. Since the preparation of thiazolium salts in which $R^1$, $R^2$, $R^3$, $R^4$ and $R^5$ have such additional substituents is generally rather costly, because costly starting materials have to be used as a rule, the use of the thiazolium or benzothiazolium ylides prepared therefrom in the process according to the invention is generally less preferred for reasons of cost. It is advantageous and preferred to use in the process according to the invention in particular thiazolium ylides of the formula Ic and polynuclear aromatic thiazolium ylides such as benzothiazolium ylides Id or naphthothiazolium ylides. The naphthothiazolium ylides of the formula II

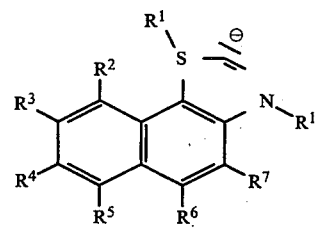

are particularly preferably used, where $R^6$ to $R^7$ have the same meanings as indicated for $R^2$ to $R^5$. It is particularly advantageous to use in the process according to the invention the thiazolium ylides Ic, the benzothiazolium ylides Id and the naphthothiazolium ylides II or the precursors thereof, the corresponding thiazolium salts, with lipophilic radicals $R^1$, especially those in which $R^1$ is $C_{10}$–$C_{20}$ alkyl. Long-chain radicals $R^1$ are, in particular, able to increase the lipophilicity of the thiazolium salts and of the thiazolium ylide catalysts prepared therefrom and thus increase the solubility thereof in the organic solvent of the two-phase system used according to the invention.

The thiazolium, benzothiazolium and naphthothiazolium ylides can also be attached to a polymeric, organic or inorganic support, for example a crosslinked styrene/divinylbenzene resin or a phenol/formaldehyde resin, e.g. via the radical $R^1$, where $R^1$ can be $C_1$–$C_{25}$, preferably $C_1$–$C_4$, alkylene.

There are various possibilities for the generation of the thiazolium ylide catalysts. Thus, the relevant thiazolium ylides can be generated in solution by heating the inner, betaine-like thiazolium salts of the formula III

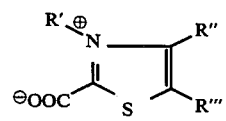

with elimination of carbon dioxide.

Another possibility comprises direct synthesis of benzothiazolium ylides Id by reacting the corresponding N-formyl-N-alkyl-o-mercaptoaniline derivatives IV with water-abstracting agents such as orthoformates as shown in equation (1)

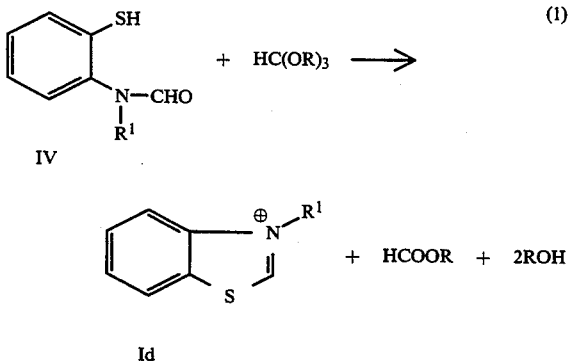

The compounds IV are formed when the N-alkyl-o-mercaptoanilines are reacted with formic acid and derivatives thereof, such as formates and orthoformates. The o-mercaptoanilines used as starting materials for preparing these compounds can be obtained, for example, by the process of DE-C 367 346. R in the orthoformates is preferably $C_1$–$C_4$-alkyl.

Another possibility for generating thiazolium ylide catalysts I comprises heating the water or alcohol adducts Ib (R=H or $C_1$–$C_{20}$ alkyl, $C_6$–$C_{12}$ aryl) in solution, in which case water or the relevant alcohol is eliminated from these adducts, usually at from 100° to 250° C. and expediently under the autogenous pressure of the reaction system.

Another method for preparing the thiazolium ylide catalysts I comprises deprotonation of the corresponding thiazolium compounds such as those of the formula V

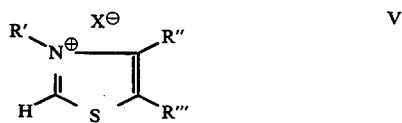

where the counter-anion $X^-$ can be, for example, a halide, nitrate, perchlorate, tetrafluoroborate, toluenesulfonate, methanesulfonate or benzenesulfonate, hydrogen sulfate or acetate ion, with the aid of bases.

Thiazolium salts of this type can easily be obtained by the generally applicable process of Matsumoto et al. (J. Am. Chem. Soc. 106 (1984) 4829) by reacting the relevant thiazoles, benzothiazoles, phenanthrothiazoles and naphthothiazoles with alkyl halides. The relevant thiazoles can be synthesized by conventional methods (see, for example, G. Vernin, General Synthetic Methods for Thiazole and Thiazolium Salts, in: Thiazole and its Derivatives (The Chemistry of Heterocyclic Compounds, Vol. 34, part I ) , Ed.: J. V. Metzger, John Wiley, New York (1979)). The alkyl halides can easily be obtained from the corresponding fatty alcohols, e.g. by treatment thereof with hydrogen halides.

The naphthothiazoles can be prepared, for example, by the process of Wanzlick et al., Liebigs Ann. Chem. 708 (1967) 155.

Examples of bases which can be used to generate the thiazolium ylides are tertiary amines with 3–30 carbons or cyclic amines as described, for example, in EP-A 219 317, which are able, because of their base strength, to deprotonate the relevant thiazolium salts in position 2 of the thiazolium ring.

Examples of suitable tertiary amines are trimethylamine, triethylamine, tripropylamine, tributylamine, ethyldiisopropylamine, decyldiethylamine, tridecylamine, quinuclidine, 1,4-diazabicyclo[2.2.2]octane, N-methylpiperidine, N-ethylpiperidine, N-propyl-piperidine, N-butylpiperidine, N,N'-dimethylpiperazine, N-methylmorpholine, dimethylbenzylamine, dibenzylmethylamine, benzyldioctylamine, benzyldiethylamine, cyclohexyldiethylamine, dicyclohexylmethylamine, dicyclohexylethylamine etc. Triethylamine is particularly preferably used. The cyclic amidines which are preferably used are 1,5-diazabicyclo[4.3.0]non-5-ene, 1,8-diazabicyclo[5.4.0]undec-7-ene and 7-methyl-1,5,7-triazabicyclo[4.4.0]dec-5-ene.

It is also possible to use polymeric tertiary amines as bases, for example crosslinked styrene/divinylbenzene resins or phenol/formaldehyde resins which have sidechains with tertiary amino groups or whose aryl groups are substituted by dialkylamino groups. Polymeric amines of this type are normally used as anion exchangers.

It is remarkable that it is particularly easy in the liquid two-phase system used according to the invention for lipophilic thiazolium salts such as hexadecylbenzothiazolium salts to be deprotonated to the corresponding catalytically active thiazolium ylides and therefore to be catalytically active even in the acid pH range. Thus, even weakly basic nitrogen compounds such as pyridine or N-alkylimidazoles, especially N-$C_1$–$C_4$-alkylimidazoles, can be used to deprotonate the thiazolium salts. Furthermore, inorganic bases such as alkali metal and alkaline earth metal carbonates or bicarbonates can be used to generate the thiazolium ylide catalysts. It is likewise possible to use alkali metal and alkaline earth metal hydroxide solutions. It is possible and advantageous to use solutions of the basic alkali metal carboxylates, in which case the sodium and potassium salts of $C_1$–$C_4$ carboxylic acids are generally preferred.

The thiazolium ylide catalysts can be generated from the said precursors by the abovementioned methods in situ in the aqueous/organic 2-phase system used according to the invention, but it may also be advantageous to generate the thiazolium ylide catalysts in a separate reaction using the said methods, to isolate them and to add the isolated pure thiazolium ylide catalysts as such to the reaction system according to the invention. One process for obtaining pure thiazolium ylide catalysts is described in German Patent Application P 41 22 669.0, to which reference is hereby made.

The process according to the invention can be carried out in a wide temperature range, for example from 20° to 160° C., preferably from 60° to 150° C. and particularly preferably from 100° to 150° C., expediently under the autogenous pressure of the reaction system used.

The pH of the aqueous phase is generally adjusted to a value below 8, preferably of from 2 to 7, in particular from 3 to 6, and kept in this range during the reaction. Use of these pH ranges in the preparation of DHA in a 2-phase system according to the invention has the advantage that thiazolium ylide catalysts are stable to attack by water on their catalytically active center. Unexpectedly, the high catalytic activity of the thiazolium ylide catalysts is retained even at these low pH values so that the catalytic activity is not impaired by acidic by-products of the reaction, for example, carboxylic acids. Thus, it is possible and advantageous to carry out the condensation of formaldehyde to DHA in the acid pH range in the process according to the invention.

EXAMPLES

EXAMPLE 1

10.06 g of a 37% by weight aqueous formaldehyde solution (Formalan ®), 10.2 g of dodecanol and 1.099 g of N-hexadecylbenzothiazolium ylide are introduced into a glass pressure vessel and stirred at 140° C. for 30 minutes. After the reaction mixture has been cooled to room temperature, the aqueous phase contained 30.4% by weight of DHA, corresponding to a yield of 82%.

EXAMPLES 2 TO 4

Examples 2 to 4 show that the process according to the invention can be carried out with a variety of thiazolium ylide catalysts.

Mixture: 4.86 g (60 mmol) of Formalin ® (37% strength), 5.0 g of 2-ethylhexanol, 0.155 g (1.5 mmol) of triethylamine and 1.5 mmol of catalyst A, B or C.

For accurate dosage of the triethylamine, 50 g of Formalin ® were mixed with 1.55 g of triethylamine, and 5.0 g of this were used immediately. The various mixtures were each vigorously stirred at 100° C. for 1 h. A sample was taken from the aqueous phase after 15, 30 and 60 minutes in each case, and the DHA content therein was determined by gas chromatography (GC). The results for Examples 2 to 4 are listed in the following table I.

TABLE I

| Ex. No. | Catalyst*) | Temp. (°C.) | Time (min) | DHA (% by wt. in solution) | Yield (%) |
| --- | --- | --- | --- | --- | --- |
| 2 | A | 100 | 15 | 4.00 | 10.8 |
|  | A | 100 | 30 | 4.96 | 13.4 |
|  | A | 100 | 60 | 7.04 | 19.0 |
| 3 | B | 100 | 15 | 0.74 | 2.0 |
|  | B | 100 | 30 | 1.34 | 3.6 |
|  | B | 100 | 60 | 2.54 | 6.9 |
| 4 | C | 100 | 15 | 18.44 | 49.8 |
|  | C | 100 | 30 | 28.81 | 77.9 |
|  | C | 100 | 60 | 26.92 | 72.7 |

*)A = N-hexadecylthiazolium bromide
B = N-hexadecylbenzothiazolium bromide
C = N-hexadecylnaphthothiazolium bromide

EXAMPLES 5 TO 14

Examples 5 to 14 show that various solvents can be used in the process according to the invention.

A mixture of 4.86 g (60 mmol) of Formalin ® (37% strength), 5.0 g of solvent, 0.155 g (1.5 mmol) of triethylamine and 0.585 g of N-hexadecylthiazolium bromide was vigorously stirred at 100° C. for 30 minutes. After the reaction was complete, the DHA content in the aqueous phase was determined by HPLC. The results of this series of experiments are listed in Table II.

TABLE II

| Ex. No. | Solvent | Time (mins) | Dihydroxyacetone (% by wt. in solution) |
| --- | --- | --- | --- |
| 5 | n-Hexanol | 30 | 1.70 |
| 6 | n-Octanol | 30 | 3.38 |
| 7 | n-Decanol | 30 | 4.62 |
| 8 | n-Dodecanol | 30 | 5.23 |
| 9 | n-Hexadecanol | 30 | 6.54 |
| 10 | Cyclohexanol | 30 | 1.06 |
| 11 | 1,12-Dodecanediol | 30 | 1.01 |
| 12 | 2-Ethylhexanol | 30 | 4.96 |
| 13 | Dibutylformamide | 30 | 2.52 |
| 14 | Dibutylformamide/n-octanol 1:1 | 30 | 3.55 |

EXAMPLES 15 TO 21

This series of experiments demonstrates that the thiazolium salt used as catalyst in the process according to the invention can be activated, ie. converted into a catalytically active thiazolium ylide, by a wide spectrum of organic and inorganic bases. It must be emphasized in particular that even weak bases such as pyridine are able under the phase-transfer conditions used to deprotonate, and thus activate, the catalyst, which is not possible under homogeneous reaction conditions.

A mixture of 4.86 g (60 mmol) of Formalin ®, 5.0 g of ethylhexanol, 1.5 mmol of base and 0.585 g (1.5 mmol) of N-hexadecylthiazolium bromide was vigorously stirred at 100° C. for 30 minutes. After this the DHA content in the aqueous phase was determined by GC. The results of this series of experiments are to be found in Table III.

TABLE III

| Ex. No. | Base | Reaction time (minutes) | DHA (% by wt. in the solution) |
| --- | --- | --- | --- |
| 15 | NaHCO$_3$ | 30 | 5.23 |
| 16 | Na$_2$CO$_3$ | 30 | 3.02 |
| 17 | Sodium acetate | 30 | 13.41 |
| 18 | Sodium formate | 30 | 7.28 |
| 19 | Pyridine | 30 | 3.25 |
| 20 | N-Methylimidazole | 30 | 7.43 |
| 21 | NaOH | 30 | 4.99 |

We claim:

1. In a process for the preparation of dihydroxyacetone by the condensation of formaldehyde in the presence of a thiazolium ylide catalyst, the improvement which comprises:

forming a two-phase liquid reaction mixture consisting of an aqueous phase in which the formaldehyde is preferentially dissolved and at least one water-immiscible organic phase which essentially contains said thiazolium ylide catalyst, and carrying out the condensation reaction by vigorously stirring and maintaining the two phases together without removal of water to promote a phase-transfer catalysis between said two phases, the pH of said aqueous phase being adjusted to maintain a value of from 2 to 7 for said reaction.

2. A process as claimed in claim 1, wherein an aqueous solution of formaldehyde is used as starting material as said aqueous phase.

3. A process as claimed in claim 1, wherein an alcohol with more than 4 carbons, or a mixture of an alcohol of this type with an organic solvent which is immiscible with water is used as organic phase.

4. A process as claimed in claim 1, wherein the reaction is carried out at from 20° to 180° C.

5. A process as claimed in claim 1, wherein lipophilic thiazolium ylides are used as catalysts.

6. A process as claimed in claim 1, wherein naphthothiazolium ylides are used as catalysts.

7. A process as claimed in claim 1, wherein the reaction is carried out at a pH of from 3 to 6.

8. A process as claimed in claim 1, wherein the ratio by volume of said aqueous phase to said organic phase is from 0.01 to 5.

9. A process as claimed in claim 1, wherein the ratio by volume of said aqueous phase to said organic phase is from 0.1 to 1.

10. A process as claimed in claim 1, wherein the ratio by volume of said aqueous phase to said organic phase is from 0.2 to 0.5, the reaction temperature is from 100° to 150° C. and the pH value is kept in a range of from 3 to 6.

11. A process as claimed in claim 1, wherein the active catalyst is lipophilic compound selected from the group consisting of the N-substituted $C_{10}$–$C_{20}$-alkyl thiazolium, benzothiazolium and naphthothiazolium ylides.

12. A process as claimed in claim 11, wherein the active catalyst is an N-($C_{10}$–$C_{20}$-alkyl)-thiazolium ylide.

13. A process as claimed in claim 11, wherein the active catalyst is an N-($C_{10}$–$C_{20}$-alkyl)-naphthothiazolium ylide.

* * * * *